(12) United States Patent
Lu et al.

(10) Patent No.: US 7,601,864 B1
(45) Date of Patent: Oct. 13, 2009

(54) METHOD FOR SYNTHESIZING 4,4-DIHALOGEN-2-(DIALKYLAMINO)METHYLENE-3-OXY-ALKYLBUTYRATE AND DERIVATIVES THEREOF

(75) Inventors: Ling Lu, Taoyuan Hsien (TW);
Shu-Cheng Liao, Taipei Hsien (TW);
Ching-Hung Chen, Taichung (TW);
Yu-Sen Hou, Kaohsiung Hsien (TW);
Kai-Chiang Huang, Taoyuan Hsien (TW); Yu-Chin Lee, Taipei (TW)

(73) Assignee: UFC Corporation, Taiwan ( * ) Notice: Subject to any disclaimer, the term of this patent is extended or adjusted under 35 U.S.C. 154(b) by 0 days.

(21) Appl. No.: 12/149,796

(22) Filed: May 8, 2008

(51) Int. Cl.
*C07C 229/00* (2006.01)
(52) U.S. Cl. ...................................... 560/170
(58) Field of Classification Search ........................ None
See application file for complete search history.

(56) References Cited

U.S. PATENT DOCUMENTS

| | | | |
|---|---|---|---|
| 2,987,491 A | 6/1961 | Bader et al. | |
| 4,027,037 A | 5/1977 | Siegle et al. | |
| 4,046,803 A | 9/1977 | Heckles | |
| 4,319,024 A | 3/1982 | Peeters et al. | |
| 4,723,031 A | 2/1988 | Lo | |
| 4,772,711 A | 9/1988 | Englaender et al. | |
| 4,877,783 A * | 10/1989 | Milner | 514/194 |
| 2006/0252944 A1 * | 11/2006 | Lantzsch et al. | 548/369.4 |

FOREIGN PATENT DOCUMENTS

| | | |
|---|---|---|
| CA | 728187 | 2/1966 |
| DE | 2938872 A1 | 4/1981 |
| DE | 3037086 A1 | 5/1982 |
| EP | 1000926 A1 | 5/2000 |

OTHER PUBLICATIONS

Richard W. Frank, et al, "Compression Effects in 1,4-Di-t-butylnaphthalenes. Chemistry and Nuclear Magnetic Resonance Spectra", Journal of Organic Chemistry, 1968, vol. 33, pp. 811-816.
Masahiro Terado et al. "Anomalous Role of Molecular Sieves 4A in the Preparation of Abinaphthol-Derived Active $\mu_3$-oxo Titanium Catalyst" Chemistry Communications, 1997, pp. 281-282.
Robert M. Hanson et al., "Procedure for the Catalytic Asymmetric Epoxidation of Allylic Alcohols in the Presence of Molecular Sieves", Journal of Organic Chemistry, 1986, vol. 51, pp. 1922-1925.
Koichi Narasaka et al., "The Asymmetric Diels-Alder Reaction by the Use of a Catalytic Amount of a Chiral Titanium Reagent", Chemistry Letters, 1986, pp. 1967-1968.
Koichi Mikami et al., "Asymmetric Glyoxylate-Ene Reaction Catalyzed by Chiral Titanium Complexes: A Practical Access to $\alpha$-Hydroxy Esters in High Enantiomeric Purities" Journal of the American Chemistry Society, 1989, vol. 111, pp. 1940-1941.

* cited by examiner

*Primary Examiner*—Paul A Zucker
(74) *Attorney, Agent, or Firm*—Fei-Fei Chao; Andrews Kurth LLP

(57) ABSTRACT

A method for synthesizing 4,4-dihalogen-2-(dialkylamino) methylene-3-oxy-alkylbutyrate and its derivatives has acts of: (a) providing N,N-dialkylamino-alkyl-acrylate in a reaction vessel; (b) adding organic alkali, organic solvent and multiple molecular sieves into the reaction vessel; (c) mixing N,N-dialkylamino-alkyl-acrylate, the organic alkali, the organic solvent and the molecular sieves; and (d) adding 2,2-dihalogen-acetyl-chloride into the reaction vessel and allowing a synthetic reaction of 2,2-dihalogen-acetyl-chloride and N,N-dialkylamino-alkyl-acrylate to obtain 4,4-dihalogen-2-(dialkylamino)methylene-3-oxy-alkylbutyrate. The molecular sieves are able to remove water efficiently to prevent materials in the reaction vessel from undergoing side reactions or changing chemical properties. Furthermore, the molecular sieves are able to adsorb chloride to avoid polymerization reactions for improved yield.

18 Claims, 6 Drawing Sheets

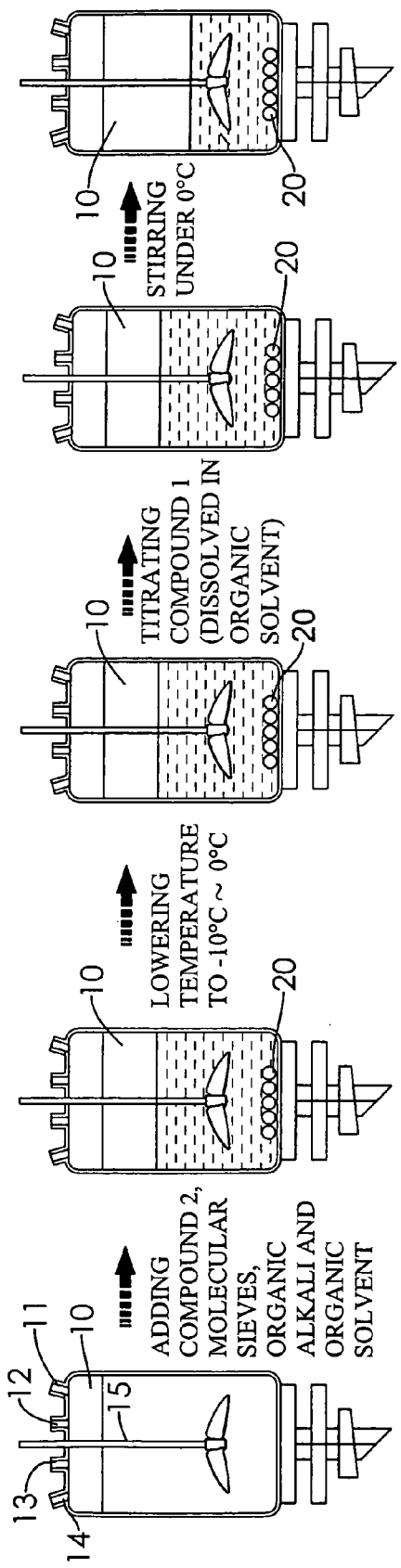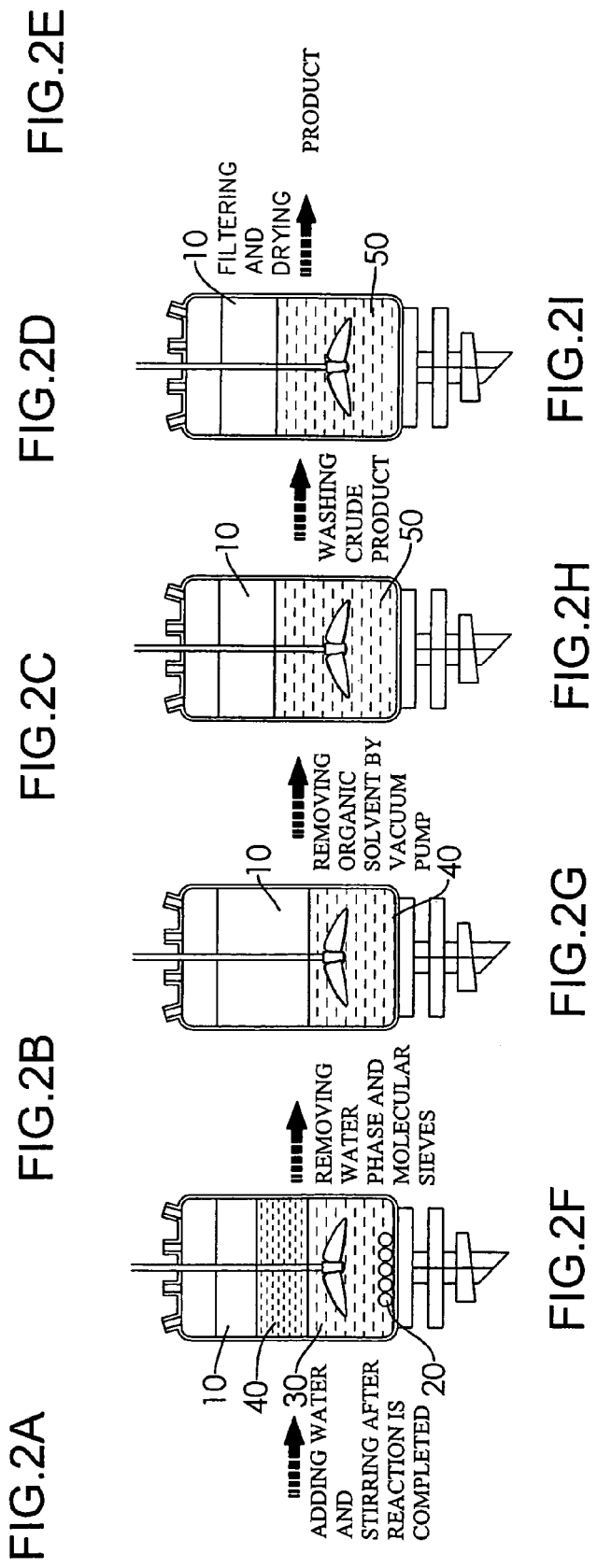

METHOD FOR SYNTHESIZING 4,4-DIHALOGEN-2-(DIALKYLAMINO)METHYLENE-3-OXY-ALKYLBUTYRATE AND DERIVATIVES THEREOF

BACKGROUND OF THE INVENTION

1. Field of Invention

The present invention relates to a method for synthesizing 4,4-dihalogen-2-(dialkylamino)methylene-3-oxy-alkyl butyrate and its derivatives, and more particularly to a method using molecular sieves to remove water and adsorb chloride of hydrochloric acid for a removal of chloride to avoid generating by-product, so yield of product can be increased.

2. Description of the Related Art 4,4-dichloro-2-(dimethylamino)methylene-3-oxy-ethylbutyrate (DDMOEB) and its derivatives are an intermediate with halogen and multiple functional groups. Because the functional groups are able to modify molecules during an organic synthesis, DDMOEB and its derivatives are suitable for synthesizing active intermediates of medicine or agricultural chemicals such as insecticide. Therefore, DDMOEB and its derivatives play important roles in medicine and agricultural fields.

U.S. Pat. No. 2,987,491, U.S. Pat. No. 4,027,037, U.S. Pat. No. 4,046,803, U.S. Pat. No. 4,319,024, U.S. Pat. No. 4,723,031, U.S. Pat. No. 4,772,711, US2006/0252944A1, DE 2,938,872, DE 3,037,086, CA 0,728,187 and EP 1,000,926 A1, disclose methods for synthesizing DDMOEB and its derivatives. These conventional syntheses use inorganic alkaline water, primary and secondary amine or other organic alkaline compounds at −20° C. to 30° C., and then require complicated and time-consuming purification to obtain the product. Overall, these conventional methods have the following shortcomings:

(1) Raw material for the synthesis is 2,2-dichloroacetyl chloride and its derivatives have an α-hydrogen. Therefore, if conditions of the synthesis are not controlled well, the synthesis produces multiple by-products. Therefore, a yield of DDMOEB and its derivatives is reduced (yield: 20% to 40%) (EP 1,000,926 A1 and Journal of Organic Chemistry 1968, vol. 33, p. 816).

(2) Synthesis is in a two-phase system, so reaction between two phases does not reach completion.

(3) Hydrochloric acid is generated from the organic alkaline compound during synthesis, which leads to a competing polymerization reaction rather than synthesizes product (Journal of Organic Chemistry 1968, vol. 33, p. 816).

(4) The synthesis produces water, which makes the synthesis complex.

(5) Temperature is hard to control because the temperature is increased from −20° C. to 50° C. during synthesis.

(6) After synthesis, a crude product undergoes purification. However, the crude product is in an emulsion so is difficult to purify, therefore the purification takes time and easily generates by-product to further decrease the yield of DDMOEB and its derivatives.

(7) A lot of organic solvent is used during purification, which contaminates the environment.

The conventional methods are inefficient with low yields, so DDMOEB produced by the conventional methods is expensive and so is not good for industry. To overcome the shortcomings, the present invention provides a method for synthesizing DDMOEB and its derivatives to mitigate or obviate the aforementioned.

Chemistry Communications 1997, p. 281-282, Journal of Organic Chemistry 1986, vol. 51, p. 1922, Chemistry Letter 1986, p. 1967-1968, and Journal of the American Chemical Society 1989, vol. 111, p. 1940 disclose a property of sodium calcium aluminosilicate to remove water efficiently and prevents accumulation of hydrochloric acid by removal of chloride. Therefore, the inventor utilizes properties of sodium calcium aluminosilicate to synthesize 4,4-dihalogen-2-(dialkylamino)methylene-3-oxy-alkylbutyrate and its derivatives.

SUMMARY OF THE INVENTION

The primary objective of the present invention is to provide a method for synthesizing 4,4-dihalogen-2-(dialkylamino) methylene-3-oxy-alkylbutyrate (DDMOEB) and its derivatives using molecular sieves to remove water and adsorb chloride ($Cl^-$) of hydrochloride for a removal of chloride to avoid generating by-products for improved yield and simplified purification.

To achieve the objective, a method for synthesizing DDMOEB and its derivatives in accordance with the present invention comprises acts of: (a) providing N,N-dialkylamino-alkyl-acrylate in a reaction vessel; (b) adding organic base, organic solvent and multiple molecular sieves into the reaction vessel; (c) mixing N,N-dialkylamino-alkyl-acrylate, the organic base, the organic solvent and the molecular sieves; and (d) adding 2,2-dihalogen-acetyl-chloride into the reaction vessel and allowing a synthetic reaction of 2,2-dihalogen-acetyl-chloride and N,N-dialkylamino-alkyl-acrylate to obtain 4,4-dihalogen-2-(dialkylamino)methylene-3-oxy-alkylbutyrate. The molecular sieves are able to remove water efficiently to prevent materials in the reaction vessel from undergoing side reactions or changing chemical properties. Furthermore, the molecular sieves are able to adsorb chloride to avoid polymerization reactions for improved yield.

Other objectives, advantages and novel features of the invention will become more apparent from the following detailed description when taken in conjunction with the accompanying drawings.

BRIEF DESCRIPTION OF THE DRAWINGS

FIG. 2 is another flow chart of a method for synthesizing 4,4-dihalogen-2-(dialkylamino)methylene-3-oxy-alkylbutyrate (DDMOEB) and its derivatives in FIG. 1;

DETAILED DESCRIPTION OF THE INVENTION

Figure 1:
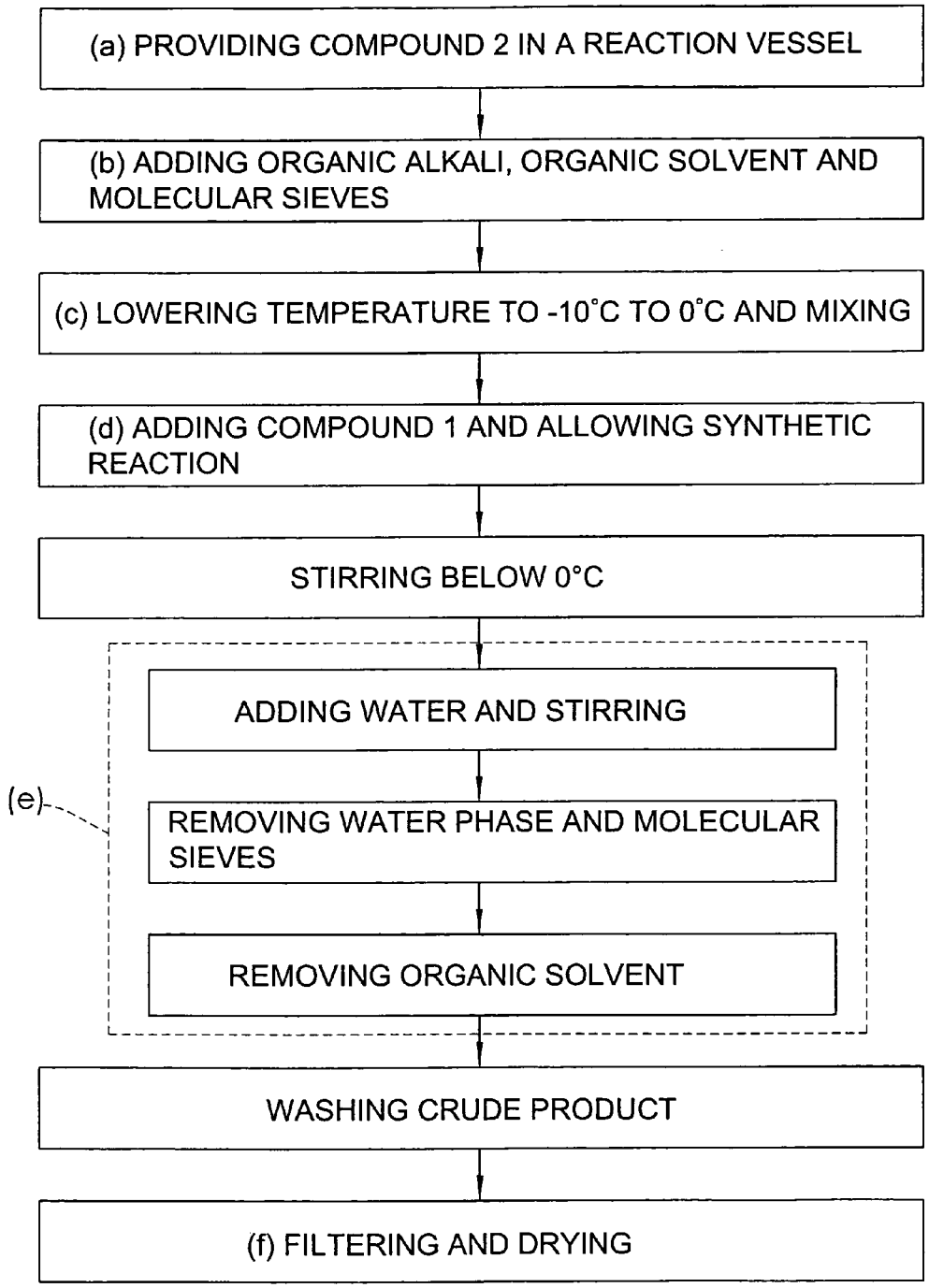
FIG. 1 is a flow chart of a method for synthesizing 4,4-dihalogen-2-(dialkylamino)methylene-3-oxy-alkylbutyrate (DDMOEB) and its derivatives in accordance with the present invention.

With reference to FIGS. 1 and 2, a method for synthesizing 4,4-dihalogen-2-(dialkylamino)methylene-3-oxy-alkylbutyrate (DDMOEB) and its derivatives comprises acts of (a) providing N,N-dialkylamino-alkyl-acrylate (compound 2) in a reaction vessel; (b) adding organic base, organic solvent and multiple molecular sieves (20) into the reaction vessel; (c) mixing N,N-dialkylamino-alkyl-acrylate, the organic base, the organic solvent and the molecular sieves (20); (d) adding 2,2-dihalogen-acetyl-chloride (compound 1) into the reaction vessel (10) and allowing a synthetic reaction of 2,2-dihalogen-acetyl-chloride and N,N-dialkylamino-alkyl-acrylate; (e) performing solvent extraction; and (f) filtering and drying to obtain 4,4-dihalogen-2-(dialkylamino)methylene-3-oxy-alkylbutyrate (compound 3) and its derivatives. The synthetic reaction of the present invention has the following chemical equation:

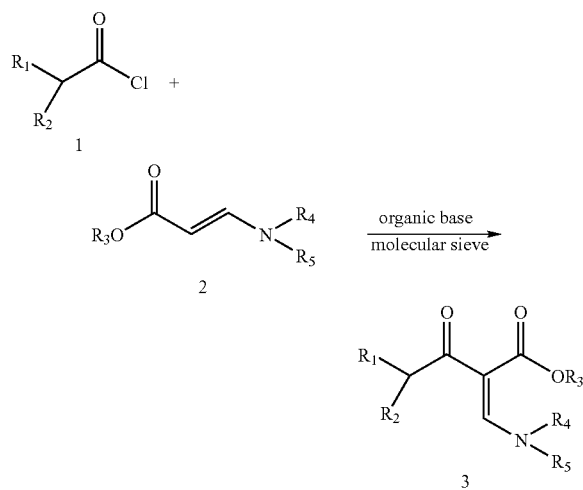

wherein $R_1$, $R_2$ are halogens and may be respectively selected from the group consisting of fluorine (F), chlorine (Cl) and bromine (Br); and $R_3$, $R_4$, $R_5$ are respectively selected from the group consisting of one to five carbon ($C_1$ to $C_5$) alkyl group (that may be selectively substituted with one to five carbon alkoxyl group), benzene group (that may comprise halogen substituent) and one to five carbon ($C_1$ to $C_5$) phenyl alkyl group.

4,4-dihalogen-2-(dialkylamino)methylene-3-oxy-alkylbutyrate derivatives refers to 4,4-dihalogen-2-(dialkylamino)methylene-3-oxy-alkylbutyrate with various $R_1$, $R_2$, $R_3$, $R_4$ and $R_5$.

Preferably $R_1$ and $R_2$ are both chlorine (Cl).

Preferably $R_3$ is an ethyl group.

Preferably $R_4$ and $R_5$ are both methyl group.

The reaction vessel (10) in the act of (a) may be a separatory funnel and has a gas inlet (11), a material inlet (12), a temperature controller (13), a condenser tube (14) and a stirrer (15) (shown in FIG. 2A).

The act of (b) adding organic base, organic solvent and multiple molecular sieves, comprises adding organic base that is selected from the group consisting of 2-ethylpyridine, 2-ethyl-1,4-diazine, triethylamine, tributyl amine and its derivatives, organic solvent that is selected from the group consisting of benzene, toluene and xylene and multiple molecular sieves (20) that are spherical and have an average pore size between 3 Å and 5 Å; and introducing nitrogen gas into the reaction vessel (10) from the gas inlet (11). Preferably the molecular sieves (20) are porous sodium calcium aluminosilicate with an average pore size of 4 Å (shown in FIG. 2B).

As used herein, a "molecular sieve" refers to a porous material that is able to adsorb gas, liquid, ion or the like. The molecular sieves of the present invention are mainly used to adsorb chloride ($Cl^-$).

The act of (c) mixing, comprises mixing N,N-dialkylamino-alkyl-acrylate, the organic base, the organic solvent and the molecular sieves (20) at a temperature between $-10°$ C. to 0° C. and stirring above materials for about 10 to 30 minutes (shown in FIG. 2C).

The act of (d) adding 2,2-dihalogen-acetyl-chloride (compound 1) into the reaction vessel (10) from the material inlet (12) and allowing a synthetic reaction comprises dissolving 2,2-dihalogen-acetyl-chloride into organic solvent that is the same as the organic solvent in the act of (b); and adding the organic solvent with 2,2-dihalogen-acetyl-chloride into the reaction vessel (10) in a nitrogen atmosphere by titration technique over 30 to 40 minutes and stirring 2,2-dihalogen-acetyl-chloride, N,N-dialkylamino-alkyl-acrylate, the organic base, the organic solvent and the molecular sieves at a temperature between $-20°$ C. to 20° C., preferably between $-10°$ C. to 10° C., until the synthetic reaction is completed (shown in FIGS. 2D and 2E). In one aspect, stirring may take about 1 to 3 hours. The synthetic reaction is detected by thin layer chromatography (TLC) to check when the reaction is complete. 2,2-dihalogen-acetyl-chloride and the organic base are in a weight ratio between 1:0.5 and 1:2.5. 2,2-dihalogen-acetyl-chloride and the molecular sieves (20) are in a weight ratio between 1:0.5 and 1:2.0.

The act of (e) performing solvent extraction comprises adding water to the reaction vessel (10) to allow a solution in the reaction vessel (10) to separate into two phases (30, 40), wherein a lower phase is a water phase (30) with the molecular sieves (20) and an upper phase is an organic-solvent phase (40); and removing the water phase (30) with the molecular sieves (20) and removing the organic solvent using a vacuum pump to obtain a crude product (50) (shown in FIGS. 2F, 2G and 2H).

The act of (f) filtering and drying comprises washing the crude product (50) with an alkyl solvent having six to nine carbons ($C_6$ to $C_9$); filtering the alkyl solvent with the crude product (50) by centrifuge to obtain a white filtrate; and drying the filtrate in a vacuum oven for about 5 to 8 hours to obtain a white solid being 4,4-dihalogen-2-(dialkylamino)methylene-3-oxy-alkyl butyrate (compound 3). The alkyl solvent with six to nine carbon is selected from the group consisting of hexane, heptane, octane, nonane and isomers thereof (shown in FIG. 2I).

The method of the present invention using molecular sieves has advantages as follows:

(1) The molecular sieves are able to remove water efficiently to prevent side reactions and materials in the reaction vessel from changing chemical properties.

(2) The molecular sieves are able to adsorb chloride to prevent accumulation of hydrochloric and avoid side reactions generating by-product so increasing yield.

(3) The molecular sieves are porous, so the solution in the reaction vessel in the act of (e) separates easily into two phases. Therefore, an amount of the organic solvent used for separating the solution can be reduced to avoid polluting environment.

(4) The molecular sieves can be reused after soaking, washing and drying using oven at 120° C., which saves costs and decreases environmental contamination.

EXAMPLES

The following examples illustrate and exemplify the present invention and compare the methods of the present invention and the prior art. Therefore, these examples of the present invention should not be considered as limitations of the present invention, but merely teach those skilled in the art how to perform the synthetic reaction of the present invention.

In the following examples, purity of a product was detected using gas chromatography (type: Shimadzu GC-2010 available from Shimadzu Corporation). Conditions of gas chromatography are shown in Table 1.

TABLE 1

| Equipment | Shimadzu GC-2010 |
|---|---|
| Solvent | Toluene |
| Column | ZB-5 (30 m * 0.32 mm) |
| Injector | 180° C. |
| Detector | 208° C. |
| Column Velocity | 1.0 ml/min |
| Injection Volume | 1.0 µl |
| Split Ratio | 30 |
| Operational Temperature | 180° C.(3 min) → 10° C./min → 280° C.(7 min) |

In the following examples, whether a synthesis reaction was completed or not was analyzed and determined by thin layer chromatography (TLC). A mobile phase of TLC is ethyl acetate and hexane (volume ration 1:1) and $R_f$ value is 0.6.

Example 1

Reaction with No Molecular Sieve 250 g (1.75 mole) of N,N-dimethylamino-ethyl-acrylate, 187.5 g (1.75 mole) of 2-ethylpyridine and 1.5 L of toluene were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethylpyridine and toluene were stirred for 10 minutes. 257.4 g (1.75 mole) of 2,2-dichloro-acetyl-chloride was dissolved in 500 mL of toluene and titrated to the reaction vessel in 30 minutes before being stirred for 3 hours at 0° C. to allow a synthetic reaction to proceed. TLC was used to analyze if N,N-dimethylamino-ethyl-acrylate was consumed to determine when an end point was achieved (wherein the end point indicates the synthesis reaction is finished). At the end point, 2 L of deionized water was added to the reaction vessel and contents of the reaction vessel was stirred for 30 minutes. After being stirred, the solution was left until two phases had separated. However, the solution was difficult remained as an emulsion. Therefore, the solution left for another 3 hours and then a water phase was removed and toluene was removed by vacuum pump to obtain a crude product. Next, the crude product was stirred and washed twice with 1 L hexane respectively and was filtered by a centrifuge. After being filtered, the crude product was dried in a vacuum oven for 5 hours to obtain a white product, 4,4-dichloro-2-(dimethylamino) methylene-3-oxy-alkyl butyrate (266 g; yield: 60%; purity: 85%; melting point: 72° C.).

Example 2

Reaction with 3 Å Molecular Sieve 248 g (1.73 mole) of N,N-dimethylamino-ethyl-acrylate, 186 g (1.73 mole) of 2-ethylpyridine, 1.5 L of toluene and 250 g of 3 Å molecular sieves (that are UOP type 3 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethylpyridine and toluene were stirred for 10 minutes. 255.3 g (1.73 mole) of 2,2-dichloro-acetyl-chloride was dissolved in 500 mL of toluene and titrated into the reaction vessel in 30 minutes and then stirred for 1.5 hours at 0° C. to allow a synthetic reaction to proceed. TLC was used to analyze if N,N-dimethylamino-ethyl-acrylate was consumed to determine an end point. Once the end point was reached, 2 L of deionized water was added to the reaction vessel and contents of the reaction vessel were stirred for 30 minutes. After being stirred, the contents immediately separated into two phases. A water phase and the 3 Å molecular sieves were removed and toluene was removed by vacuum pump to obtain a crude product. Next, the crude product was stirred and washed twice with 1 L hexane respectively and was filtered by a centrifuge. After being filtered, the crude product was dried in a vacuum oven for 5 hours to obtain a white product, 4,4-dichloro-2-(dimethylamino)methylene-3-oxy-alkylbutyrate (330 g; yield: 75%; purity: 99.1%; melting point: 67° C.).

Example 3

Figure 3:
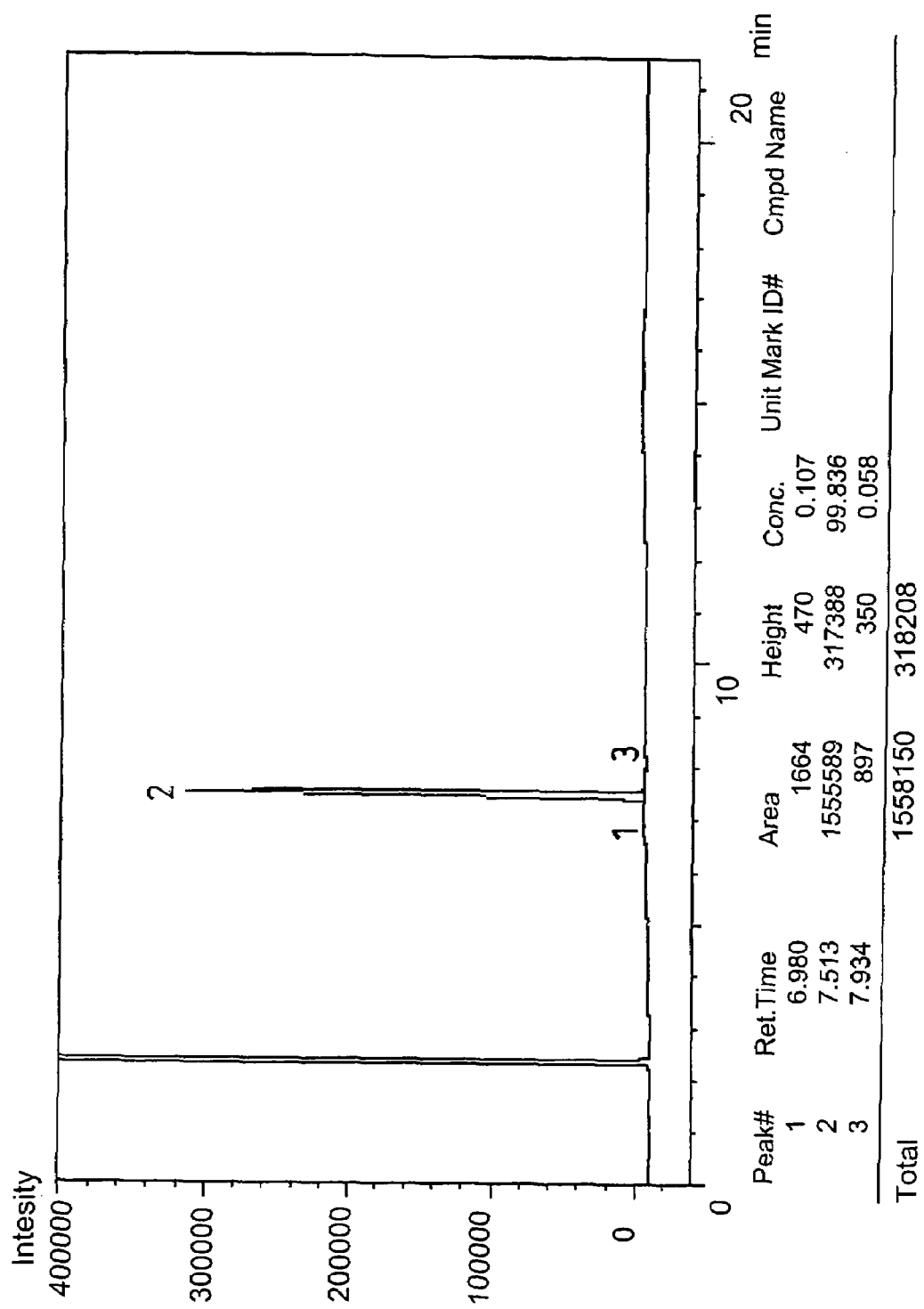
FIG. 3 is a gas chromatography (GC) chromatogram of DDMOEB of example 3 in accordance with the present invention.
Figure 4:
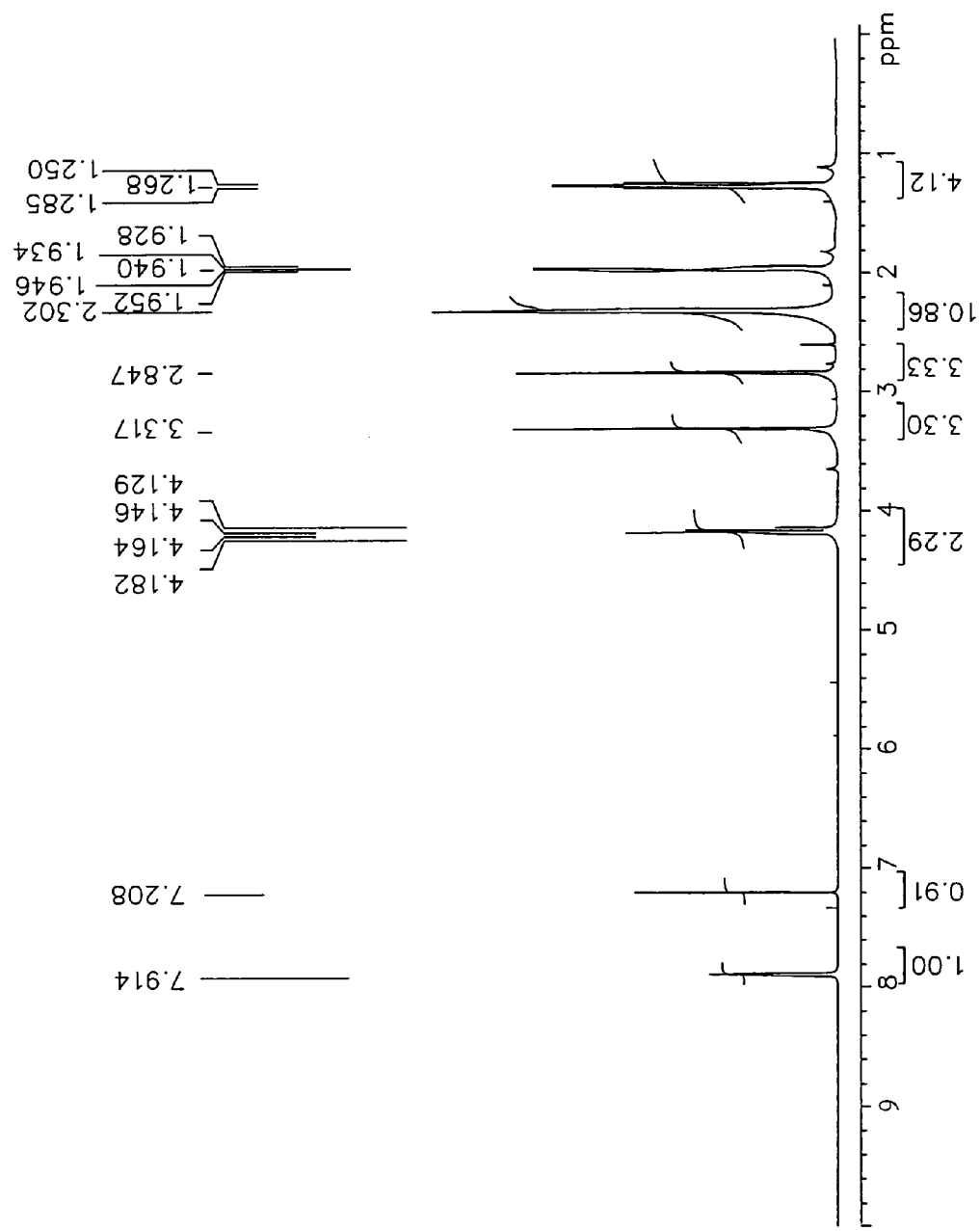
FIG. 4 is a Proton-NMR ($^1$H-NMR) spectrum of DDMOEB of example 3 in accordance with the present invention.
Figure 5:
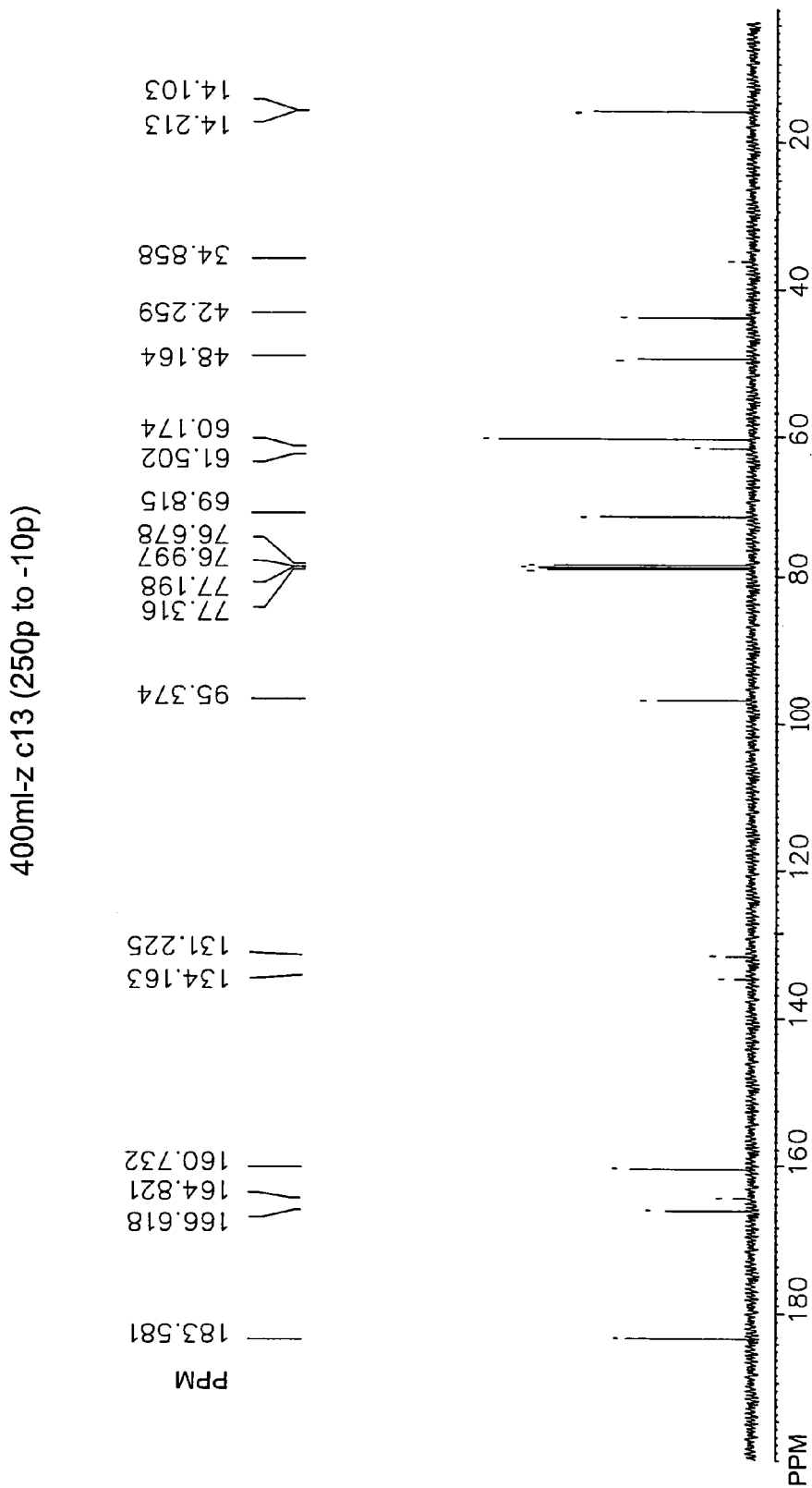
FIG. 5 is a Carbon-NMR ($^{13}$C-NMR) spectrum of DDMOEB of example 3 in accordance with the present invention.
Figure 6:
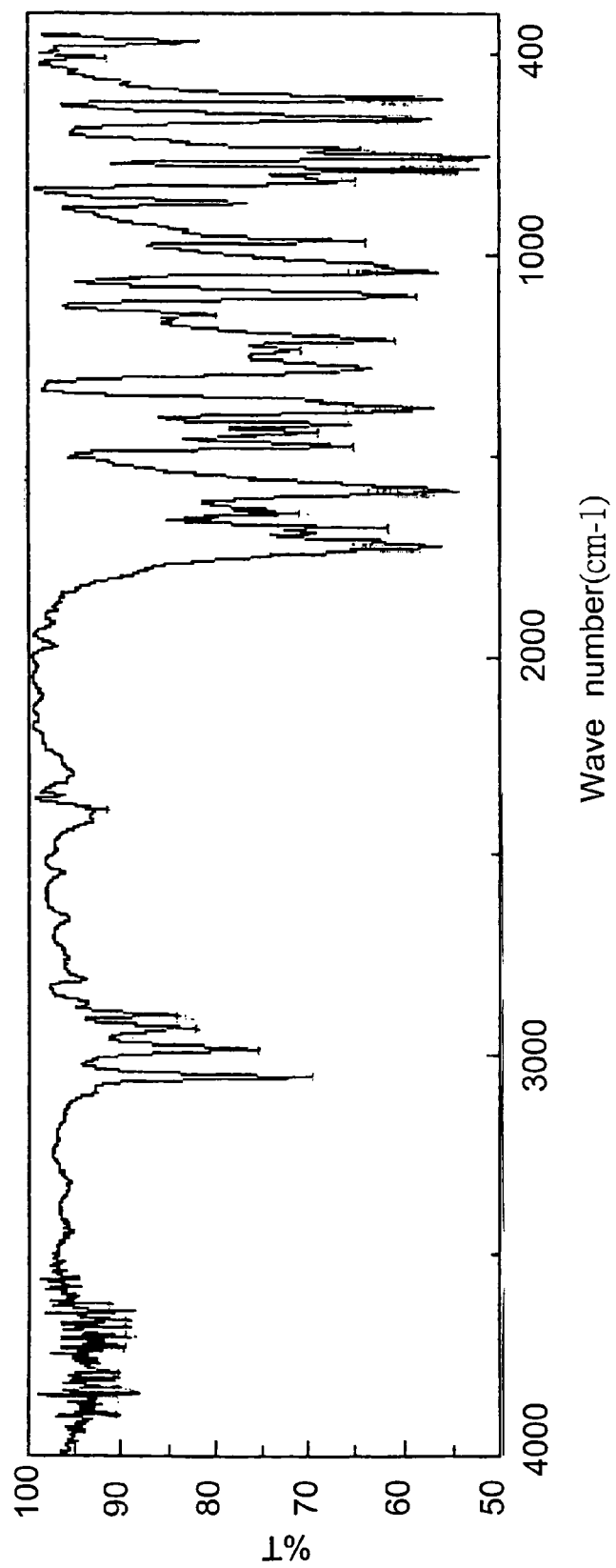
FIG. 6 is a frustrated total internal reflection (FTIR) spectrum of DDMOEB of example 3 in accordance with the present invention.

Reaction with 4 Å Molecular Sieve 245 g (1.71 mole) of N,N-dimethylamino-ethyl-acrylate, 183.3 g (1.71 mole) of 2-ethylpyridine, 1.5 L of toluene and 250 g of 4 Å molecular sieves (that are UOP type 4 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethylpyridine and toluene were stirred for 10 minutes. 252.2 g (1.71 mole) of 2,2-dichloro-acetyl-chloride was dissolved in 500 mL of toluene and titrated into the reaction vessel in 30 minutes and then stirred for 1.5 hours at 0° C. to allow a synthetic reaction to proceed. TLC was used to analyze if N,N-dimethylamino-ethyl-acrylate was consumed to determine if the synthetic reaction had reached an end point. Once the end point was reached, 2 L of deionized water was added to the reaction vessel and contents of the reaction vessel were stirred for 30 minutes. After being stirred, the contents immediately separated into two phases. Then, a water phase and the 4 Å molecular sieves were removed and toluene was removed by vacuum pump to obtain a crude product. Next, the crude product was stirred, washed twice with 1 L hexane respectively and filtered by centrifuge. After being filtered, the crude product was dried in a vacuum oven for 5 hours to obtain a white product being 4,4-dichloro-2-(dimethylamino)methylene-3-oxy-alkyl butyrate (395.7 g; yield: 91%; purity: 99.8% (as shown in FIG. 3); melting point: 68° C.). The structure of the product was analyzed by $^1$H-NMR, $^{13}$C-NMR and frustrated total internal reflection (FTIR), which are respectively shown in FIGS. 4, 5 and 6.

The 4 Å molecular sieves were soaked in 1 L of isopropanol for 24 hours, then dried at 120° C. for 24 hours to obtain 245 g of 4 Å molecular sieves (recycling rate: 98%).

Example 4

Reaction with 5 Å Molecular Sieve 230 g (1.6 mole) of N,N-dimethylamino-ethyl-acrylate, 172.1 g (1.6 mole) of 2-ethylpyridine, 1.5 L of toluene and 250 g of 5 Å molecular sieves (that are UOP type 5 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethylpyridine and toluene were stirred for 10 minutes. 235.8.2 g (1.6 mole) of 2,2-dichloro-acetyl-chloride was dissolved in 500 mL of toluene and titrated into the reaction vessel in 30 minutes and then stirred for 1.5 hours at 0° C. to allow a synthetic reaction to proceed. TLC was used to analyze if N,N-dimethylamino-ethyl-acrylate was consumed to determine an end point. Once the end point was reached, 2 L of deionized water was added to the reaction vessel contents of the reaction vessel were stirred for 30 minutes. After being stirred, the contents immediately separated into two phases. Then, a water phase and the 5 Å molecular sieves were removed and toluene was removed by vacuum pump to obtain a crude product. Next, the crude product was stirred and washed twice with 1 L hexane respectively and filtered by a centrifuge. After being filtered, the crude product was dried in a vacuum oven for 5 hours to obtain a white product being 4,4-dichloro-2-(dimethylamino)methylene-3-oxy-alkyl butyrate (342.8 g; yield: 84%; purity: 99.0%; melting point: 67° C.).

Example 5

Reaction with No Molecular Sieve 200 g (1.4 mole) of N,N-dimethylamino-ethyl-acrylate, 141.3 g (1.4 mole) of triethylamine and 1.5 L of toluene were added sequentially to a 5-liter reaction vessel. Then, nitrogen was introduced to the reaction vessel, an operation temperature in the reaction vessel was lowered to −10° C. and N,N-dimethylamino-ethyl-acrylate, triethylamine and toluene were stirred for 10 minutes. 206.3 g (1.4 mole) of 2,2-dichloro-acetyl-chloride was dissolved in 500 mL of toluene and titrated into the reaction vessel in 30 minutes and then stirred for 2 hours at 0° C. to allow a synthetic reaction to proceed. TLC was used to analyze if N,N-dimethylamino-ethyl-acrylate was consumed to determine an end point. Once the end point was reached, 500 mL of deionized water was added to the reaction vessel and contents of the reaction vessel were stirred for 30 minutes. After being stirred, the solution was left to settle until the contents had separated into two phases. However, the contents remained as an emulsion. Therefore, the contents were left for another 4 hours and then a water phase was removed and toluene was removed by vacuum pump to obtain a crude product. Next, the crude product was stirred and washed twice with 1.5 L hexane respectively and was filtered by a centrifuge. After being filtered, the crude product was dried in a vacuum oven for 10 hours to obtain a white product, 4,4-dichloro-2-(dimethylamino)methylene-3-oxy-alkyl butyrate (88 g; yield: 25%; purity: 74%; melting point: 74° C.).

Example 6

Reaction with 4 Å Molecular Sieve 220 g (1.54 mole) of N,N-dimethylamino-ethyl-acrylate, 155.5 g (1.54 mole) of 2-ethyl-1,4-diazine, 1.5 L of toluene and 250 g of 4 Å molecular sieves (that are UOP type 4 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethyl-1,4-diazine and toluene were stirred for 10 minutes. 226.5 g (1.54 mole) of 2,2-dichloro-acetyl-chloride was dissolved in 500 mL of toluene and titrated into the reaction vessel in 30 minutes and then was stirred for 2 hours at 0° C. to allow a synthetic reaction to proceed. TLC was used to analyze if N,N-dimethylamino-ethyl-acrylate was consumed to determine an end point. Once the end point was reached, 2 L of deionized water was added to the reaction vessel and contents of the reaction vessel was stirred for 30 minutes. After being stirred, the contents immediately separated into two phases. Then, a water phase and the 4 Å molecular sieves were removed and toluene was removed by vacuum pump to obtain a crude product. Next, the crude product was stirred and washed twice with 1.5 L hexane respectively and was filtered by centrifuge. After being filtered, the crude product was dried in a vacuum oven for 5 hours to obtain a white product, 4,4-dichloro-2-(dimethylamino)methylene-3-oxy-alkylbutyrate (250 g; yield: 64%; purity: 95%; melting point: 69° C.).

The 4 Å molecular sieves were soaked in 2 L of isopropanol for 24 hours, then was dried at 120° C. for 24 hours to obtain 245 g of 4 Å molecular sieves (recycling rate: 98%).

Example 7

Reaction with No Molecular Sieve 230 g (1.61 mole) of N,N-dimethylamino-ethyl-acrylate, 174.1 g (1.61 mole) of 2-ethyl-1,4-diazine and 1.5 L of xylene were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethyl-1,4-diazine and xylene were stirred for 20 minutes. 237.3 g (1.61 mole) of 2,2-dichloro-acetyl-chloride was dissolved in 500 mL of xylene and titrated into the reaction vessel in 40 minutes and then stirred for 4 hours at −5° C. to allow a synthetic reaction to proceed. TLC was used to analyze if N,N-dimethylamino-ethyl-acrylate was consumed to determine and end point. Once the end point was reached, contents of the reaction vessel were heated to 10° C. 2.5 L of deionized water was added to the reaction vessel and the contents of the reaction vessel was stirred for 40 minutes. After being stirred, the contents was left to settle until the contents had separated into two phases. However, the solution remained as an emulsion. Therefore, 500 mL of deionized water was added and the contents were left to settled for a further 3 hours, then a water phase was removed and xylene was removed by vacuum pump to obtain a crude product. Next, the crude product was stirred and washed twice with 1.5 L n-heptane respectively and was filtered by centrifuge. After being filtered, the crude product was dried in a vacuum oven for 8 hours to obtain a white product, 4,4-dichloro-2-(dimethylamino)methylene-3-oxy-alkyl butyrate (265.8 g; yield: 65%; purity: 90%; melting point: 70° C.).

Example 8

Reaction with 3 Å Molecular Sieve 244 g (1.7 mole) of N,N-dimethylamino-ethyl-acrylate, 183.8 g (1.7 mole) of 2-ethyl-1,4-diazine, 1.5 L of xylene and 250 g of 3 Å molecular sieves (that are UOP type 3 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethyl-1,4-diazine and xylene were stirred for 30 minutes. 250.6 g (1.7 mole) of 2,2-dichloro-acetyl-chloride was dissolved in 500 mL of xylene and titrated into the reaction vessel in 40 minutes and then was stirred for 3 hours at −5° C. to allow a synthetic reaction to proceed. TLC was used to analyze if N,N-dimethylamino-ethyl-acrylate was consumed to determine an end point. Once the end point was reached, contents of the reaction vessel were heated to 10° C. 2.5 L of deionized water was added to the reaction vessel and contents of the reaction vessel were stirred for 40 minutes. After being stirred, the contents immediately separated into two phases. Then, a water phase and the 3 Å molecular sieves were removed and xylene was removed by vacuum pump to obtain a crude product. Next, the crude product was stirred and washed twice with 1.5 Ln-heptane respectively and was filtered by a centrifuge. After being filtered, the crude product was dried in a vacuum oven for 8 hours to obtain a white product, 4,4-dichloro-2-(dimethylamino)methylene-3-oxy-alkyl butyrate (320 g; yield: 74%; purity: 99.1%; melting point: 67° C.).

The 3 Å molecular sieves were soaked in 2 L of isopropanol for 24 hours then dried at 120° C. for 24 hours to obtain 243 g of 3 Å molecular sieves (recycling rate: 97.2%).

Example 9

Reaction with 4 Å Molecular Sieve 250 g (1.75 mole) of N,N-dimethylamino-ethyl-acrylate, 189.2 g (1.75 mole) of 2-ethyl-1,4-diazine, 1.5 L of xylene and 250 g of 4 Å molecular sieves (that are UOP type 4 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethy-lamino-ethyl-acrylate, 2-ethyl-1,4-diazine and xylene were stirred for 30 minutes. 257.4 g (1.75 mole) of 2,2-dichloro-acetyl-chloride was dissolved in 500 mL of xylene and titrated into the reaction vessel in 40 minutes and then stirred for 3 hours at −5° C. to allow a synthetic reaction to proceed. TLC was used to analyze if N,N-dimethylamino-ethyl-acrylate was consumed to determine an end point. Once the end point was reached, contents of the reaction vessel were heated to 10° C. 2.5 L of deionized water was added to the reaction vessel and the contents of the reaction vessel were stirred for 40 minutes. After being stirred, the contents immediately separated into two phases. Then, a water phase and the 4 Å molecular sieves were removed and xylene was removed by vacuum pump to obtain a crude product. Next, the crude product was stirred and washed twice with 1.5 L n-heptane respectively and was filtered by centrifuge. After being filtered, the crude product was dried in a vacuum oven for 8 hours to obtain a white product, 4,4-dichloro-2-(dimethy-lamino)methylene-3-oxy-alkylbutyrate (400.2 g; yield: 90%; purity: 99.5%; melting point: 68° C.).

The 4 Å molecular sieves were soaked in 2 L of isopropanol for 24 hours then dried at 120° C. for 24 hours to obtain 245 g of 4 Å molecular sieves (recycling rate: 98%).

Example 10

Reaction with 5 Å Molecular Sieve 247 g (1.73 mole) of N,N-dimethylamino-ethyl-acrylate, 187 g (1.73 mole) of 2-ethyl-1,4-diazine, 1.5 L of xylene and 250 g of 5 Å molecular sieves (that are UOP type 5 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, 2-ethyl-1,4-diazine and xylene were stirred for 30 minutes. 255 g (1.73 mole) of 2,2-dichloro-acetyl-chloride was dissolved in 500 mL of xylene and titrated into the reaction vessel in 40 minutes and stirred for 3 hours at −5° C. to allow a synthetic reaction to proceed. TLC was used to analyze if N,N-dimethylamino-ethyl-acrylate was consumed to determine an end point. Once the end point was reached, contents of the reaction vessel were heated to 10° C. 2.5 L of deionized water was added to the reaction vessel and the contents of the reaction vessel was stirred for 40 minutes. After being stirred, the contents immediately separated into two phases. Then, a water phase and the 5 Å molecular sieves were removed and xylene was removed by vacuum pump to obtain a crude product. Next, the crude product was stirred and washed twice with 1.5 L n-heptane respectively and filtered by centrifuge. After being filtered, the crude product was dried in a vacuum oven for 8 hours to obtain a white product, 4,4-dichloro-2-(dimethylamino)methylene-3-oxy-alkylbutyrate (378.1 g; yield: 86%; purity: 99.1%; melting point: 68° C.).

The 5 Å molecular sieves were soaked in 2 L of isopropanol for 24 hours then dried at 120° C. for 24 hours to obtain 247 g of 5 Å molecular sieves (recycling rate: 98.8%).

Example 11

Reaction with No Molecular Sieve 218 g (1.52 mole) of N,N-dimethylamino-ethyl-acrylate, 281.7 g (1.52 mole) of tributyl amine and 1.5 L of xylene were added sequentially to a 5-liter reaction vessel. Then, nitrogen was introduced to the reaction vessel, an operation temperature in the reaction vessel was lowered to −10° C. and N,N-dimethylamino-ethyl-acrylate, tributyl amine and xylene were stirred for 30 minutes. 224 g (1.52 mole) of 2,2-dichloro-acetyl-chloride was dissolved in 500 mL of xylene and titrated into the reaction vessel in 40 minutes then stirred for 4 hours at −1° C. to allow a synthetic reaction to proceed. TLC was used to analyze if N,N-dimethylamino-ethyl-acrylate was consumed to determine an end point. Once the end point was reached, contents of the reaction vessel were heated to 10° C. 2.5 L of deionized water was added to the reaction vessel and contents of the reaction vessel were stirred for 40 minutes. After being stirred, the solution was left until the contents separated into two phases. However, the contents remained as an emulsion. Therefore, 500 mL deionized water was further added, the contents were stirred for 30 minutes and left for 4 hours then a water phase was removed and xylene was removed by vacuum pump to obtain a crude product. Next, the crude product was stirred and washed twice with 1.5 L n-heptane respectively and was filtered by centrifuge. After being filtered, the crude product was dried in a vacuum oven for 8 hours to obtain a white product, 4,4-dichloro-2-(dimethylamino)methylene-3-oxy-alkylbutyrate (193.1 g; yield: 50%; purity: 81%; melting point: 71° C.).

Example 12

Reaction with 4 Å Molecular Sieve 240 g (1.68 mole) of N,N-dimethylamino-ethyl-acrylate, 310.6 g (1.68 mole) of tributyl amine, 1.5 L of xylene and 250 g of 4 Å molecular sieves (that are UOP type 4 Å beads purchased from the Fluka Company) were added sequentially to a 5-liter reaction vessel. Then, nitrogen was introduced to the reaction vessel, an operation temperature in the reaction vessel was lowered to −10° C. and N,N-dimethylamino-ethyl-acrylate, tributyl amine and xylene were stirred for 30 minutes. 247.6 g (1.68 mole) of 2,2-dichloro-acetyl-chloride was dissolved in 500 mL of xylene and titrated into the reaction vessel in 40 minutes then stirred for 2 hours at −10° C. to allow a synthetic reaction to proceed. TLC was used to analyze if N,N-dimethylamino-ethyl-acrylate was consumed to determine an end point. After the end point was reached, contents of the reaction vessel were heated to 10° C. 2.5 L of deionized water was added to the reaction vessel and the solution in the reaction vessel was stirred for 40 minutes. After being stirred, the solution immediately separated into two phases. Then, a water phase and the 4 Å molecular sieves were removed and xylene was removed by vacuum pump to obtain a crude product. Next, the crude product was stirred and washed twice with 1.5 L n-heptane respectively and was filtered by centrifuge. After being filtered, the crude product was dried in a vacuum oven for 8 hours to obtain a white product, 4,4-dichloro-2-(dimethylamino)methylene-3-oxy-alkylbutyrate (303.1 g; yield: 71%; purity: 98%; melting point: 70° C.).

The 4 Å molecular sieves were soaked in 2 L of isopropanol for 24 hours then were dried at 120° C. for 24 hours to obtain 244 g of 4 Å molecular sieves (recycling rate: 97.6%).

According to the foregoing examples, any product produced by each of the methods of the present invention has a better yield and purity than a product produced by a method of the prior art. Therefore, the molecular sieves are proved to play an important role in synthesizing 4,4-dihalogen-2-(dialkylamino)methylene-3-oxy-alkylbutyrate. Also, less organic solvent is used to purify the product and less time is required for synthesis of the product.

Furthermore, the product in example 3 has a better yield and purity than products in other examples. Therefore, the molecular sieves preferably are 4 Å molecular sieves, the organic base is preferably 2-ethylpyridine when the organic solvent is toluene.

Even though numerous characteristics and advantages of the present invention have been set forth in the foregoing description, together with details of the structure and function of the invention, the disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A method for synthesizing 4,4-dihalogen-2-(dialkylamino) methylene-3-oxy-alkylbutyrate denoted by formula 3

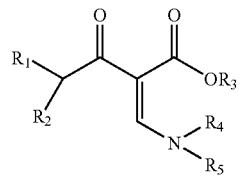

and its derivatives comprising acts of:
(a) providing N,N-dialkylamino-alkyl-acrylate denoted by formula 2

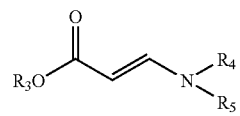

in a reaction vessel;
(b) adding organic base, organic solvent and molecular sieves to the reaction vessel;
(c) mixing N,N-dialkylamino-alkyl-acrylate, the organic base, the organic solvent and the molecular sieves; and
(d) adding 2,2-dihalogen-acetyl-chloride denoted by formula 1

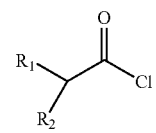

into the reaction vessel for allowing a synthetic reaction;
wherein $R_1$ and $R_2$ are respectively selected from the group consisting of fluorine, chlorine and bromine; and
$R_3$, $R_4$ and $R_5$ are respectively selected from the group consisting of $C_1$ to $C_5$ alkyl group, $C_1$ to $C_5$ phenyl alkyl group and benzene group being selectively substituted with halogens;
(e) performing solvent extraction after the step of (d) comprising
adding water into the reaction vessel to allow contents of the reaction vessel to separate into two phases, wherein a lower phase is a water phase with the molecular sieves and an upper phase is an organic-solvent phase;
removing the water phase with the molecular sieves and removing the organic solvent using a vacuum pump to obtain a crude product; and
washing the crude product by an alkyl solvent with $C_6$ to $C_9$; and
(f) filtering the alkyl solvent with the crude product to obtain a filtrate and drying the filtrate to obtain a product containing 4,4-dihalogen-2-(dialkylamino) methylene-3-oxy-alkylbutyrate and its derivatives.

2. The method according to claim 1, wherein the molecular sieves have an average pore size between 3 Å and 5 Å.

3. The method according to claim 1, wherein the organic base is selected from the group consisting of 2-ethylpyridine, 2-ethyl-1,4-diazine, triethylamine and tributyl amine.

4. The method according to claim 1, wherein the organic solvent is selected from the group consisting of benzene, toluene and xylene.

5. The method according to claim 1, wherein 2,2-dihalogen-acetyl-chloride and the organic base are in a weight ratio between 1:0.5 and 1:2.5.

6. The method according to claim 1, wherein 2,2-dihalogen-acetyl-chloride and the molecular sieves are in a weight ratio between 1:0.5 and 1:2.0.

7. The method according to claim 1, wherein the act of
(c) adding 2,2-dihalogen-acetyl-chloride into the reaction vessel comprises dissolving 2,2-dihalogen-acetyl-chloride into an organic solvent being the same as the organic solvent in the act of (b); and
adding the organic solvent with 2,2-dihalogen-acetyl-chloride into the reaction vessel in a nitrogen atmosphere over 30 to 40 minutes and stirring 2,2-dihalogen-acetyl-chloride, N,N-dialkylamino-alkyl-acrylate, the organic base, the organic solvent and the molecular sieves at a temperature between −20° C. to 20° C. until the synthetic reaction has reached an end point.

8. The method according to claim 1, wherein the alkyl solvent with six to nine carbons is selected from the group consisting of hexane, heptane, octane, nonane and isomers thereof.

9. The method according to claim 8, wherein drying the filtrate is performed in a vacuum oven for about 5 to 8 hours to obtain the product containing 4,4-dihalogen-2-(dialkylamino)methylene-3-oxy-alkylbutyrate.

10. A method for synthesizing 4,4-dichloro-2-(dimethylamino) methylene-3-oxy-alkylbutyrate denoted by formula 3:

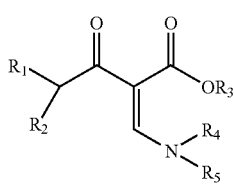

comprising acts of:
(a) providing N,N-dimethylamino-ethyl-acrylate denoted by formula 2

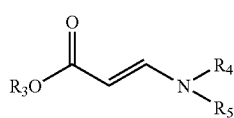

in a reaction vessel;
(b) adding organic base, organic solvent and molecular sieves to the reaction vessel, wherein $R_3$ is an ethyl group; and $R_4$ and $R_5$ are methyl groups;
(c) mixing N,N-dimethylamino-ethyl-acrylate, the organic base, the organic solvent and the molecular sieves; and
(d) adding 2,2-dichloro-acetyl-chloride denoted by formula 1

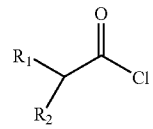

into the reaction vessel for allowing a synthetic reaction; wherein $R_1$, $R_2$ are chlorine; and
(e) performing solvent extraction, comprising acts of
adding water into the reaction vessel to allow contents of the reaction vessel after act (d) to separate into two phases, wherein a lower phase is a water phase with the molecular sieves and an upper phase is an organic-solvent phase;
removing the water phase with the molecular sieves and removing the organic solvent using a vacuum pump to obtain a crude product; and
washing the crude product by an alkyl solvent with $C_6$ to $C_9$; and
(f) filtering the alkyl solvent with the crude product to obtain a filtrate and drying the filtrate to obtain the product containing 4,4-dihalogen-2-(dialkylamino)methylene-3-oxy-alkyl butyrate.

11. The method according to claim 10, wherein the molecular sieves have an average pore size between 3 Å and 5 Å.

12. The method according to claim 10, wherein the organic base is selected from the group consisting of 2-ethylpyridine, 2-ethyl-1,4-diazine, triethylamine, tributyl amine and its derivatives.

13. The method according to claim 10, wherein the organic solvent is selected from the group consisting of benzene, toluene and xylene.

14. The method according to in claim 10, wherein 2,2-dihalogen-acetyl-chloride and the organic base are in a weight ratio between 1:0.5 and 1:2.5.

15. The method according to in claim 10, wherein 2,2-dihalogen-acetyl-chloride and the molecular sieves are in a weight ratio between 1:0.5 and 1:2.0.

16. The method according to claim 10, wherein
the act of (d) adding 2,2-dichloro-acetyl-chloride into the reaction vessel and allowing a synthetic reaction of 2,2-dichloro-acetyl-chloride and N,N-dimethylamino-ethyl-acrylate comprises dissolving 2,2-dichloro-acetyl-chloride into an organic solvent being the same as the organic solvent in the act of (b); and
adding the organic solvent with 2,2-dichloro-acetyl-chloride into the reaction vessel in a nitrogen ambiance by titration over 30 to 40 minutes and stirring 2,2-dichloro-acetyl-chloride, N,N-dimethylamino-ethyl-acrylate, the organic base, the organic solvent and the molecular sieves at a temperature between −20° C. to 20° C. until the synthetic reaction is completed.

17. The method according to claim 10, wherein the alkyl solvent with six to nine carbon is selected from the group consisting of hexane, heptane, octane, nonane and isomers thereof.

18. The method according to claim 17, wherein drying the filtrate is performed in a vacuum oven for about 5 to 8 hours to obtain the product containing 4,4-dichloro-2-(dimethylamino)methylene-3-oxy-alkylbutyrate.

* * * * *